(12) United States Patent
Hsu (10) Patent No.: US 9,438,204 B2
(45) Date of Patent: Sep. 6, 2016

(54) SIGNAL PROCESSING DEVICE AND SIGNAL PROCESSING METHOD

(71) Applicant: MEDIATEK INC., Hsin-Chu (TW)

(72) Inventor: Chien-Hua Hsu, Hsinchu County (TW)

(73) Assignee: MEDIATEK INC., Hsin-Chu (TW)

( * ) Notice: Subject to any disclaimer, the term of this patent is extended or adjusted under 35 U.S.C. 154(b) by 274 days.

(21) Appl. No.: 14/010,562

(22) Filed: Aug. 27, 2013

(65) Prior Publication Data

US 2015/0061758 A1    Mar. 5, 2015

(51) Int. Cl.

| | |
|---|---|
| *H03B 1/00* | (2006.01) |
| *H03K 5/00* | (2006.01) |
| *H04B 1/10* | (2006.01) |
| *H03H 21/00* | (2006.01) |
| *A61B 5/00* | (2006.01) |
| *A61B 5/04* | (2006.01) |
| *A61B 5/0428* | (2006.01) |

(Continued)

(52) U.S. Cl.
CPC ...... *H03H 21/0025* (2013.01); *A61B 5/04017* (2013.01); *A61B 5/0428* (2013.01); *A61B 5/0452* (2013.01); *A61B 5/7203* (2013.01); *G06K 9/0051* (2013.01); *G06K 9/0055* (2013.01); *H03H 21/0021* (2013.01); *A61B 5/725* (2013.01); *H03H 2021/0081* (2013.01); *H03H 2021/0094* (2013.01); *H03H 2210/033* (2013.01)

(58) Field of Classification Search
USPC ...... 327/552, 553, 558; 331/15–17; 341/120
See application file for complete search history.

(56) References Cited

U.S. PATENT DOCUMENTS 4,906,941 A * 3/1990 Kato et al. ............ 327/159
6,441,661 B1 * 8/2002 Aoki ............ G11B 20/1024
                                              327/150

(Continued)

FOREIGN PATENT DOCUMENTS

| CN | 1032288 A | 4/1989 |
|---|---|---|
| CN | 1596825 A | 3/2005 |
| CN | 102215040 A | 10/2011 |
| DE | 103 58 397 A1 | 7/2005 |
| EP | 1 995 685 A2 | 11/2008 |
| EP | 1995685 A2 | 11/2008 |

(Continued)

OTHER PUBLICATIONS

Vessela Krasteva et al., Assessment of ECG frequency and morphology parameters for automatic classification of life-threatening cardiac arrhythmias, Physiological Measurement, Jun. 17, 2005, pp. 707-723, vol. 26, XP020092224, Institute of Physics Publishing, UK.

(Continued)

*Primary Examiner* — Brandon S Cole
(74) *Attorney, Agent, or Firm* — Winston Hsu; Scott Margo (57) ABSTRACT

Embodiments of the invention disclose a signal processing device and a signal processing method and a device and a method for signal processing. The signal processing device includes a sampling module, a first segmentation module, a second segmentation module, and a detection module. The sampling module samples an input signal to generate a sample signal. The first segmentation module calculates a first segment value according to the sample signal during a first time interval. The second segmentation module calculates a second segment value according to the sample signal during a second time interval different in length from the first time interval. The detection module generates a detection signal according to the determination of whether the first segment value lies out of a first range, and whether the second segment value lies out of a second range.

19 Claims, 7 Drawing Sheets

(51) Int. Cl.
  *A61B 5/0452*  (2006.01)
  *G06K 9/00*  (2006.01)

(56) References Cited

U.S. PATENT DOCUMENTS

| | | | | |
|---|---|---|---|---|
| 6,701,445 | B1* | 3/2004 | Majos | 713/500 |
| 7,054,402 | B2* | 5/2006 | Muellner | 375/355 |
| 8,542,068 | B2* | 9/2013 | Doyle et al. | 331/17 |
| 2005/0008112 | A1* | 1/2005 | Takeo et al. | 375/375 |
| 2009/0310730 | A1* | 12/2009 | Zhidkov et al. | 375/376 |
| 2010/0318151 | A1 | 12/2010 | Saha | |
| 2013/0162309 | A1* | 6/2013 | Tamura | 327/156 |
| 2014/0266824 | A1* | 9/2014 | Lowney | H03M 1/1009 341/120 |

FOREIGN PATENT DOCUMENTS

| | | |
|---|---|---|
| EP | 2 294 978 A1 | 3/2011 |
| WO | 2012129413 A1 | 9/2012 |

OTHER PUBLICATIONS

Antti Koski, Primitive coding of structural ECG features, Pattern Recognition Letters, 1996, pp. 1215-1222, vol. 17, XP004025305, Elsevier Science B.V.

Chris F. Zhang et al., VLSI Friendly ECG QRS Complex Detector for Body Sensor Networks, IEEE Journal on Emerging and Selected Topics in Circuits and Systems, Mar. 2012, pp. 52-59, vol. 2, No. 1, XP011441042, IEEE.

* cited by examiner

SIGNAL PROCESSING DEVICE AND SIGNAL PROCESSING METHOD

BACKGROUND

1. Technical Field

The invention generally relates to a device and a method for signal processing, and more particularly, to a device and a method for signal processing which can selectively initiate a reduction process according to the characteristic of noise components present within an input signal.

2. Description of Related Art

With the development of biomedical engineering, doctors are able to make convincing diagnoses according to different sorts of medical reports produced by biomedical inspection instruments. For example, the instruments may obtain a physiologic signal, such as an electrocardiogram (ECG) signal, through electrodes directly attached to a patient's chest, arm, or leg. Then, the physiological signals can be detected and transmitted to processing device for further processing.

Typically, the amplitude of the ECG signal transmitted from electrodes is usually measured around millivolts, so that noise components within the ECG signal may significantly affect the actual waveform of the ECG signal. Thus, it is almost meaningless to analyze the ECG signal with the presence of noise components in the ECG waveforms. In order to deal with this sorts of dilemma, high pass filters or band pass filters are generally used to conduct a noise reduction process to reduce the noise components caused by environment, such as power-line interference, ambient electromagnetic activity or movements of electrodes. Besides, signal processing techniques are also considered useful for reducing the noise components of the ECG signal, such as baseline wander effect and motion artifact. As reducing noise components within the ECG signal may be one of the most critical biomedical issues nowadays, it is worthy to develop a signal processing device and a signal processing method which can filter out the noise components.

SUMMARY

According to an embodiment of the invention, a signal processing device is disclosed. The signal processing device includes a sampling module, a first segmentation module, a second segmentation module, and a detection module. The sampling module samples an input signal to generate a sample signal. The first segmentation module calculates a first segment value according to the sample signal during a first time interval. The second segmentation module calculates a second segment value according to the sample signal during a second time interval, wherein the length of the first time interval is different from that of the second time interval. The detection module is coupled to the first segmentation module and the second segmentation module to generate a detection signal according to the determination of whether the first segment value lies out of a first range, and whether the second segment value lies out of a second range.

According to another embodiment of the invention, a signal processing method is disclosed. The signal processing method includes the following steps. First, a sample signal is generated by sampling an input signal. Then, a first segment value is calculated according to the sample signal during a first time interval. And, a second segment value is calculated according to the sample signal during a second time interval, wherein the length of the first time interval is different from that of the second time interval. Further, a detection signal is generated according to the determination of whether the first segment value lies out of a first range, and whether the second segment value lies out of a second range.

According to another embodiment of the invention, a signal processing device is disclosed. The signal processing device includes a sampling module, a first segmentation module, a second segmentation module, and a reduction module. The sampling module samples an input signal to generate a sample signal. The first segmentation module calculates a first segment value according to the sample signal during a first time interval. The second segmentation module calculates a second segment value according to the sample signal during a second time interval, wherein the length of the first time interval is different from that of the second time interval. The reduction module is coupled to the sampling module, the first segmentation module and the second segmentation module to generate an output signal according to the sample signal, the first segment value and the second segment value.

According to still another embodiment of the invention, a signal processing method is disclosed. The signal processing method includes the following steps. First, a sample signal is generated by sampling an input signal. Then, a first segment value is calculated according to the sample signal during a first time interval. And, a second segment value is calculated according to the sample signal during a second time interval, wherein the length of the first time interval is different from that of the second time interval. Further, an output signal is generated according to the sample signal, the first segment value and the second segment value.

In order to further the understanding regarding the invention, the following embodiments are provided along with illustrations to facilitate the disclosure of the invention.

DETAILED DESCRIPTION

The aforementioned illustrations and following detailed description are exemplary for the purpose of illustrating the invention, but not limiting the scope of the invention. Some objectives and advantages related to the invention will be illustrated in the subsequent description and appended drawings.

Figure 1:
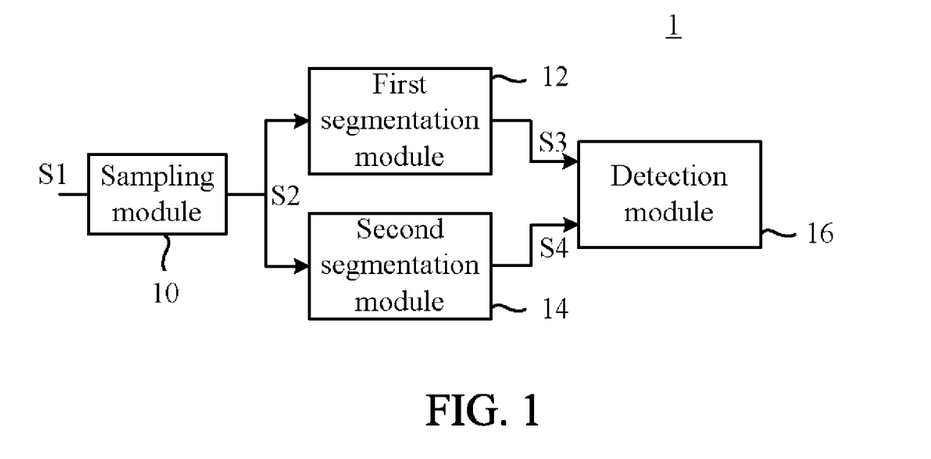
FIG. 1 shows a schematic diagram of a signal processing device according to an embodiment of the invention.

FIG. 1 shows a schematic diagram of a signal processing device according to an embodiment of the invention. As shown in FIG. 1, the signal processing device 1 includes a sampling module 10, a first segmentation module 12, a second segmentation module 14, and a detection module 16. The sampling module 10 samples an input signal 51 to generate a sample signal S2. The sample signal S2 is fed to the first segmentation module 12 and the second segmentation module 14. Then, the first segmentation module 12 calculates a first segment value S3 according to the sample signal S2 during a first time interval. And, the second segmentation module 14 calculates a second segment value S4 according to the sample signal S2 during a second time interval. The length of the first time interval is different from that of the second time interval. The detection module 16 is coupled to the first segmentation module 12 and the second segmentation module 14 to generate a detection signal according to the determination of whether the first segment value lies out of a first range, and whether the second segment value lies out of a second range.

Figure 2:
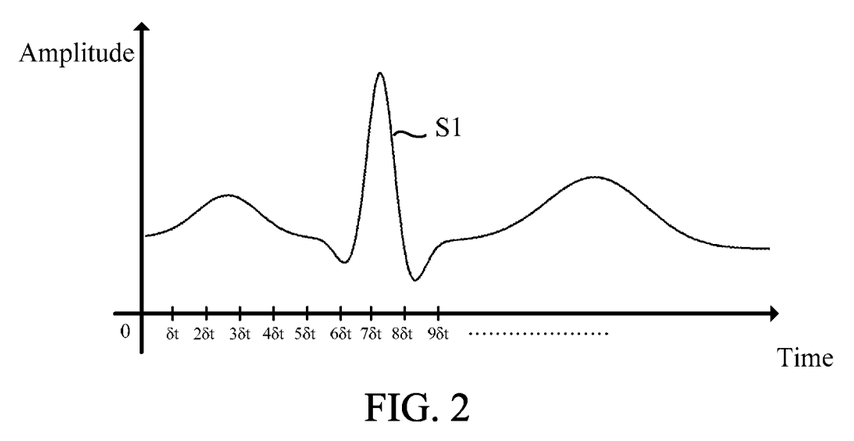
FIG. 2 shows an oscillogram of an input signal according to an embodiment of the invention.

As an example for illustrating the operation of the sampling module 10, please refer to FIG. 1 and FIG. 2. FIG. 2 is an exemplary oscillogram showing the amplitude of the input signal S1. For example, the input signal S1 may be an analog ECG signal acquired by electrodes and the sampling module 10 may be an analog-to-digital converter (ADC). As shown in FIG. 1 and FIG. 2, the sampling module 10 samples the amplitude information of input signal S1 at time instants $\delta t$, $2\delta t$, $3\delta t$, $4\delta t$, etc. to generate the sample signal S2. In other words, the sample signal S2 can be formulated as shown below:

$$S2=\{S1[\delta t], S1[2\delta t], S1[3\delta t], S1[4\delta t], \ldots\} \quad (1)$$

Note that the value of $\delta t$ should be chosen small enough to preserve the characteristic of the input signal S1. For instance, if the input signal S1 is an ECG signal, the $\delta t$ might be within several milliseconds.

Figure 3:
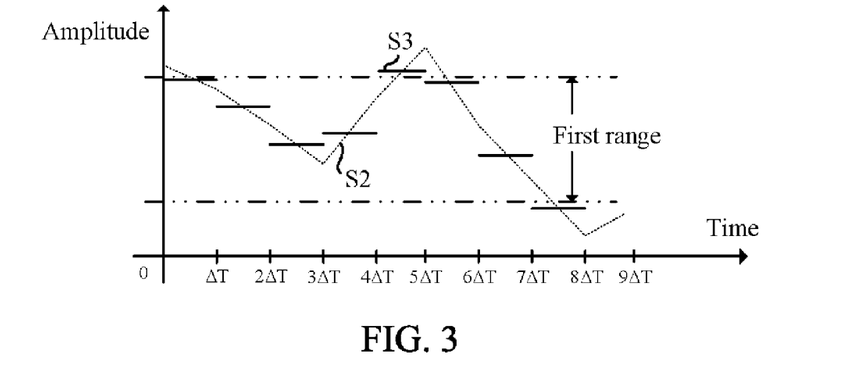
FIG. 3 shows an example waveform of a plurality of first segment values according to an embodiment of the invention.

Please refer to FIG. 1 and FIG. 3 for exemplifying the operation of the first segmentation module. FIG. 3 shows an example waveform of a plurality of first segment values S3 according to an embodiment of the invention. To be noted, the waveform of the first segment values S3 in FIG. 3 is explanatory waveform diagram, and may not necessarily be in compliance with the input signal S1 shown in FIG. 2. In FIG. 3, the solid line represents the waveform of the first segment values S3. As an example, the length of a first time interval equals to the time interval $\Delta T$ in this embodiment. And the first segmentation module 12 uses sample data of the sample signal S2 within the first time interval to derive the first segment value S3. To state it in another way, the first segmentation module 12 calculates the first segment value S3 according to the sample signal S2 during the first time interval.

In one embodiment, the first segment value S3 is generated by averaging the plurality of sample data of the sample signal S2 within the first time interval. Of course, the first segment value S3 may be calculated in other mathematical methods as long as the amplitude characteristics of the sample signal S2 is preserved. In addition, the period of the first time interval may be set by considering the characteristic of the input signal. For example, if the input signal S1 is a ECG signal with baseline wander effect, the first time interval $\Delta T$ may be approximately 100~200 ms. As such, during the first time interval $\Delta T$, there might be tens of samples of the sample signal S2.

Figure 4:
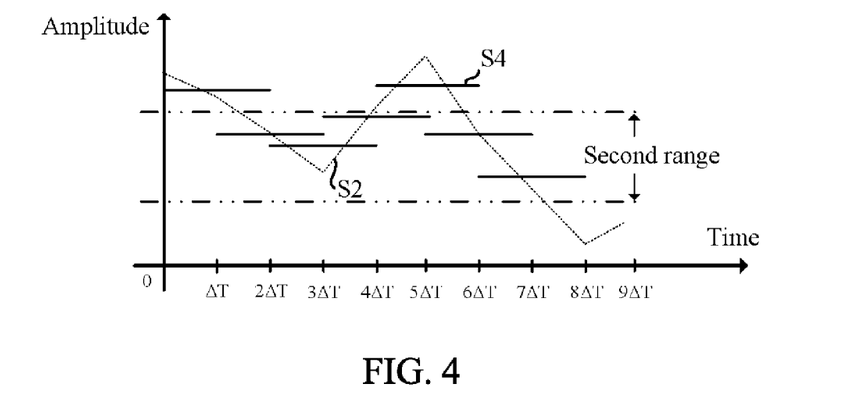
FIG. 4 shows an example waveform of a plurality of second segment values according to an embodiment of the invention.

Please refer to FIG. 1 and FIG. 4 for exemplifying the operation of the second segmentation module. FIG. 4 shows an example waveform of a plurality of second segment values S4 according to an embodiment of the invention. To be noted, the waveform of the second segment values S4 in FIG. 4 is explanatory waveform diagram, and may not necessarily be in compliance with the input signal S1 shown in FIG. 2. In FIG. 4, the solid line represents the waveform of the second segment values S4. In one embodiment, since the length of the second time interval is different from that of the first time interval, the second time interval can be set larger than the first time interval. For example, the second time interval may be equal to twice of the first time interval, i.e. $2\Delta T$. And the second segmentation module 14 uses sample data of the sample signal S2 within the second time interval to derive the second segment value S4. To state it in another way, the second segmentation module 14 calculates the second segment value S4 according to the sample signal S2 within the second time interval which is different in length from the first time interval. Note that the length of the second time interval is not limited to an integer multiple of the length of the first time interval. For instance, the second time interval can be $2.3\Delta T$.

In one embodiment, the second segment value S4 is generated by averaging the sample data of the sample signal S2 within the second time interval. Of course, the second segment value S4 may be calculated in other mathematical methods as long as the amplitude characteristics of the sample signal S2 is preserved.

Please refer to FIG. 1, FIG. 3, and FIG. 4 for illustrating the operation of the detection module 16. The detection module 16 receives the first segment value S3 from the first segmentation module 12. And, the detection module 16 receives the second segment value S4 from the second segmentation module 14. As an example, referring to FIG. 3 and FIG. 4, the first segment value S3 during the time period from $4\Delta T$ to $5\Delta T$ lies out the first range, and the corresponding contemporary second segment value S4 also lies out the second range. In this example, the first segment value S3 and the second segment value S4 are generated by averaging the sample signal S2 during the first time interval and the second time interval, respectively. The detection module 16 generates the detection signal according to the determination result. In one embodiment, the detection signal may be a tri-state signal. When the detection signal is at "1" representing that the first segment value S3 lies out of the first range, and the second segment value S4 lies out of the second range. When the detection signal is at "0" representing that either the first segment value S3 lies out of the first range, or the second segment value S4 lies out of the second range. When the detection signal is at "−1" representing that the first segment value S3 lies within the first range, and the second segment value S4 also lies within the second range.

As a common application, the input signal S1 can be an ECG signal containing different types of noise. Noise, such as motion artifact effect, might have a frequency range above 0.5 Hz while baseline wander might have a lower frequency and may affect the ECG signal for more than half a second. On the other hand, for patients with certain heart disease, the morphology of the ECG might have irregular variation, usually having higher frequency than the baseline wander effect. By properly selecting the first time interval, the second time interval, the first range and the second range, it might be helpful in distinguishing noise from the morphology variation through the first segment value and the second segment value. Generally speaking, the low frequency noise will last a longer period of time. Therefore, if a low frequency noise, e.g. baseline wander effect, exists in the ECG signal, both of the short term first segment value S3 and the long term segment value S4 will be laid out of certain amplitude ranges. Thus, the noise existence can be detected by determining whether the short term first segment value S3 lies out of the first range and the corresponding contemporary long term second segment value S4 lies out the second range. In other words, if the short term first segment value S3 lies out of the first range and the corresponding contemporary long term second segment value S4 lies out the second range, e.g. detection signal at "1", it is possible that the input signal S1 may bear a low frequency noise-like effect. If the short term first segment value S3 lies out of the first range but the corresponding contemporary long term second segment value S4 lies within the second range, e.g. detection signal at "0", it is possible that the input signal S1 may bear a disease-like effect rather than a noise-like effect. Further, if the short term first segment value S3 lies within the first range and the corresponding contemporary long term second segment value S4 lies within the second range, e.g. the detection signal at "−1", it is likely that there might be no or little noise inside the input signal S1.

Figure 5A:
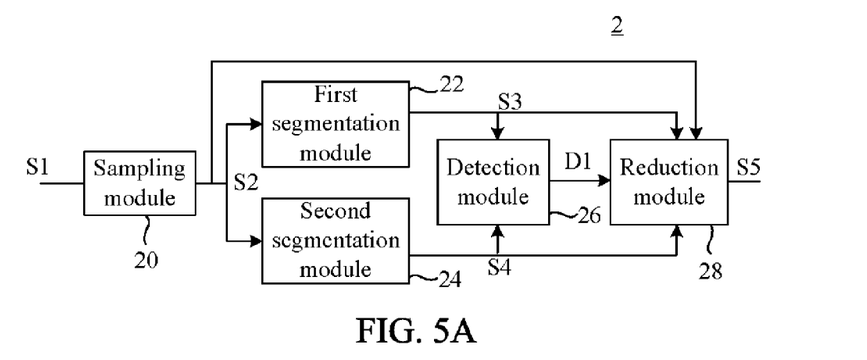
FIG. 5A shows a schematic diagram of a signal processing device according to another embodiment of the invention.

Please refer to FIG. 5A. FIG. 5A shows a schematic diagram of a signal processing device according to another embodiment of the invention. As shown in FIG. 5A, the signal processing device 2 includes a sampling module 20, a first segmentation module 22, a second segmentation module 24, a detection module 26, a reduction module 28. The sampling module 20 samples an input signal S1 to generate a sample signal S2. The first segmentation module 22 receives the sample signal S2 and calculates a plurality of first segment values S3 during a plurality of first time intervals. The second segmentation module 24 receives the sample signal S2 and calculates a plurality of second segment values S4 during a plurality of second time intervals. The length of the first time interval is different from that of the second time interval. The detection module 26 generates a detection signal D1 according to the determination of whether the first segment value S3 lies within a first range and whether the corresponding contemporary second segment value S4 lies within the second range. The reduction module 28 is coupled to the sampling module 20 and detection module 26 to receive the sample signal S2, at least one of the first segment values S3 and the second segment values S4, and the detection signal D1 to generate an output signal S5. As mentioned in the previous embodiment, the detection signal bears some varies values or levels to indicate the existence of noise. When the noise exist in the ECG signal, the reduction module 28 enters into a first state to deal with the noisy input signal S1 so as to generate the noise-reduced output signal S5. In one embodiment, if the detection signal indicates that the noise does not exist in the ECG signal, the reduction module 28 may bypass and output the sample signal S2 as the output signal S5.

Figure 6A:
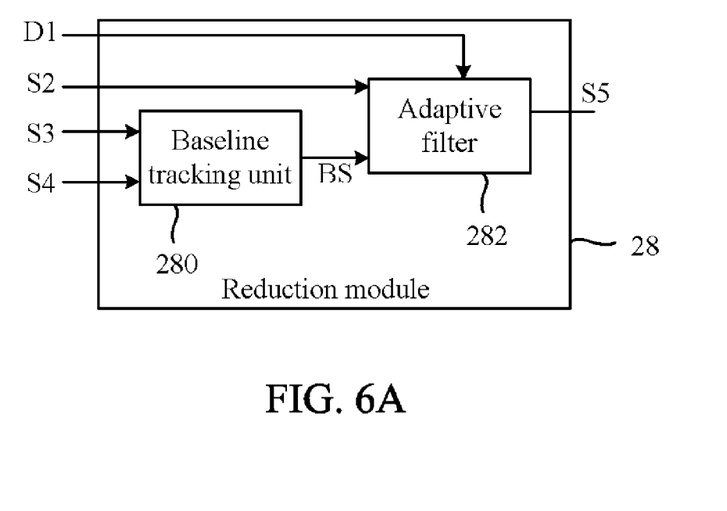
FIG. 6A shows a schematic diagram of a reduction module of the signal processing device in FIG. 5A according to an embodiment of the invention.

For better understanding the operation of the reduction module 28, please refer to FIG. 6A as an example schematic diagram of the reduction module 28. As shown in FIG. 6A, the reduction module 28 may have a baseline tracking unit 280 and an adaptive filter 282. The baseline tracking unit 280 is coupled to the first segment module 22 and the second segment module 24 in FIG. 5A to receive the plurality of first segment values S3 and the plurality of second segment values S4, and generates an estimated baseline signal BS.

The adaptive filter 282 is coupled to the baseline tracking unit 280 to receive the estimated baseline signal BS. The adaptive filter 282 also receives the sample signal S2 from the sampling module 20 and uses the estimated baseline signal BS and the sample signal S2 to generate the output signal S5. In addition, the adaptive filter 282 may further receive the detection signal D1 as another input for adjusting a step size SS of the adaptive filter 282.

In practice, the baseline tracking unit 280 may generate the estimated baseline signal BS according to at least one of the first segment values S3 and the second segment values S4, or in combination. For example, the baseline tracking unit 280 may perform interpolation over the plurality of first segment values S3 to generate the estimated baseline signal BS.

Figure 6B:
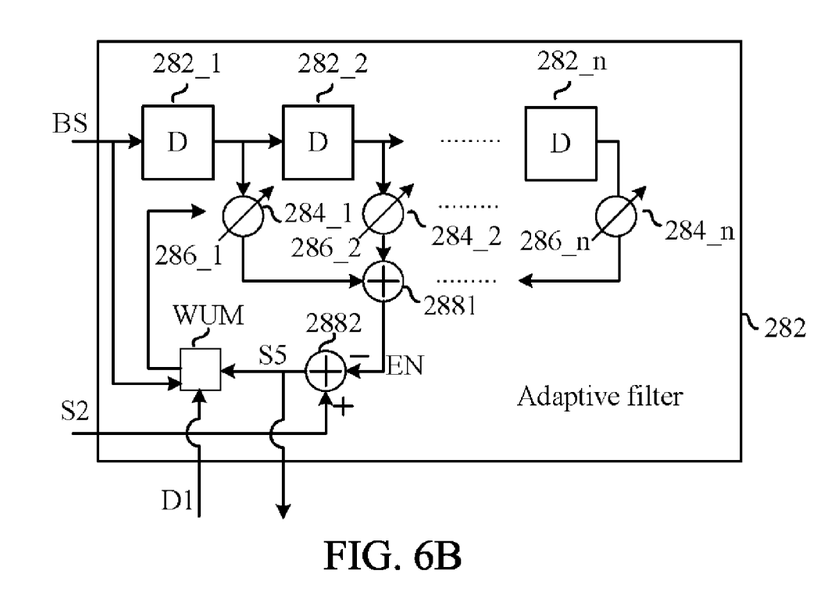
FIG. 6B shows a circuit diagram of an adaptive filter of the reduction module in FIG. 6A according to another embodiment of the invention.

In one embodiment, please refer to FIG. 6B. FIG. 6B shows an example circuit diagram of the adaptive filter 282. The adaptive filter 282 includes a plurality of delay taps 282_1~282_n, a plurality of multipliers 284_1~284_n, a first adder 2881, and a second adder 2882. The estimated baseline signal BS is fed into the delay taps and delayed by the plurality of delay taps 282_1~282_n. Each of the output of the delay taps 282_1~282_n are sent to the multipliers 284_1~284_n to multiply with a corresponding weight 286_1~286_n. The output of the multipliers 284_1~284_n are added together by the first adder 2881 to generate an estimated noise signal EN. As shown, the adaptive filter 282 is implemented by a common tapped-delay line structure with variable weights. The estimated noise signal EN is then sent to the second adder 2882 to be subtracted from the sample signal S2 to derive the output signal S5. The output signal S5 is used to update the variable weights 286_1~286_n by a weight updating module WUM which generates the updated variable weights. For example, we may get the updated variable weights by adding each of the variable weights 286_1~286_n respectively with SS*S5*BS, where SS is the step size of the adaptive filter 282 adjustable according to the detection signal D1 and the amount of weight change equals the product of SS, S5 and BS. In the ideal steady state, the estimated noise signal EN tracks the noise components of the sample signal S2 perfectly so that the estimated noise signal EN converges to the noise components in S2. When the difference of the output signal S5 and the sample signal S2 is large, e.g. the input signal S1 being affected by noise, the variable weights 286_1~286_n need to be updated faster so as to make the estimated noise signal EN to track the sample signal S2 better. Hence, the step size should be adjusted accordingly. In this embodiment, when the detection signal indicates the sample signal S2 is affected by noise, the reduction module 28 enters into the first state. The adaptive filter 282 then updates the variable weights 286_1~286_n of the filter according to a first step size while the reduction module 28 being in the first state.

As mentioned earlier, when the characteristics of the input signal S1 changes, the value of the detection signal might change. For example, when there's less noise inside the input signal S1, either the first segment values S3 lies within the first range or the corresponding contemporary of the second segment values S4 lies within the second range. In this situation, the detection signal will bear a corresponding value. The reduction module 28 then enters into a second state. And, a second step size will be adopted by the adaptive filter 282 to update the variable weights 286_1~286_n. In other words, the adaptive filter 282 then generates the output signal S5 by filtering the estimated baseline signal BS according to the second step size and the sample signal S2 while the reduction module 28 being in the second state.

To be noted, when there's no or little noise inside the input signal S1, the reduction module 28 might not enter into the first state nor the second state. In this case, the adaptive filter 282 might just bypass the sample signal S2 as the output signal S5.

As another embodiment, the estimated baseline signal BS may be directly subtracted from the sample signal S2 to generate the output signal S5. In this situation, the adaptive filter 282 is not needed and may be entirely replaced by an adder, resulting in a lower cost. Under certain operating conditions, experiments show that this approach also bear competitive performance in reducing the noise inside the sample signal S2.

Figure 5B:
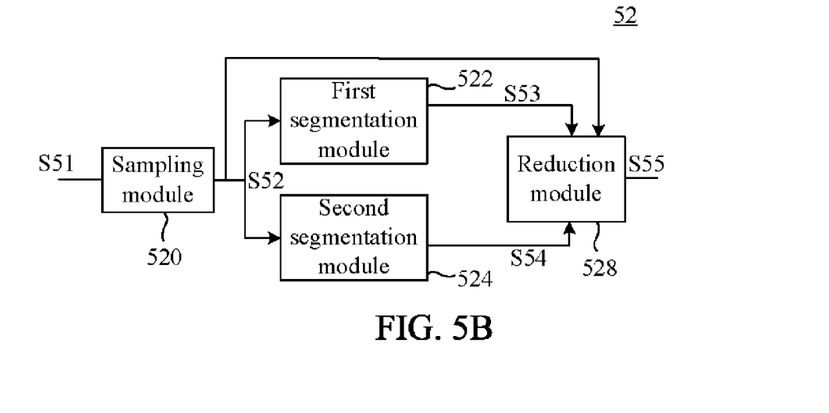
FIG. 5B shows a schematic diagram of a signal processing device according to still another embodiment of the invention.

Please refer back to FIG. 5B. FIG. 5B shows a schematic diagram of a signal processing device according to still another embodiment of the invention. As shown in FIG. 5B, the signal processing device 52 includes a sampling module 520, a first segmentation module 522, a second segmentation module 524, a reduction module 528. The sampling module 520 samples an input signal S51 to generate a sample signal S52. The first segmentation module 522 receives the sample signal S52 and calculates a plurality of first segment values S53 during a plurality of first time intervals. The second segmentation module 524 receives the sample signal S52 and calculates a plurality of second segment values S54 during a plurality of second time intervals. The length of the first time interval is different from that of the second time interval. The reduction module 528 receives the sample signal S52, the first segment value S53 and the second segment value S54 to generate an output signal S55.

In practice, the schematic diagram of the reduction module 528 may be almost the same as that shown in FIG. 6A. In other words, the reduction module 528 may also include a baseline tracking unit and an adaptive filter operating in similar style as mentioned previously. Yet, the adaptive filter may not have different states nor different step sizes but may keep filtering an estimated noise signal with a fixed step size ever since the system startup. Note that the adaptive filter may also be replaced by an adder that subtracts the estimated baseline signal directly from the sample signal S52 to generate the output signal S55.

Figure 7:
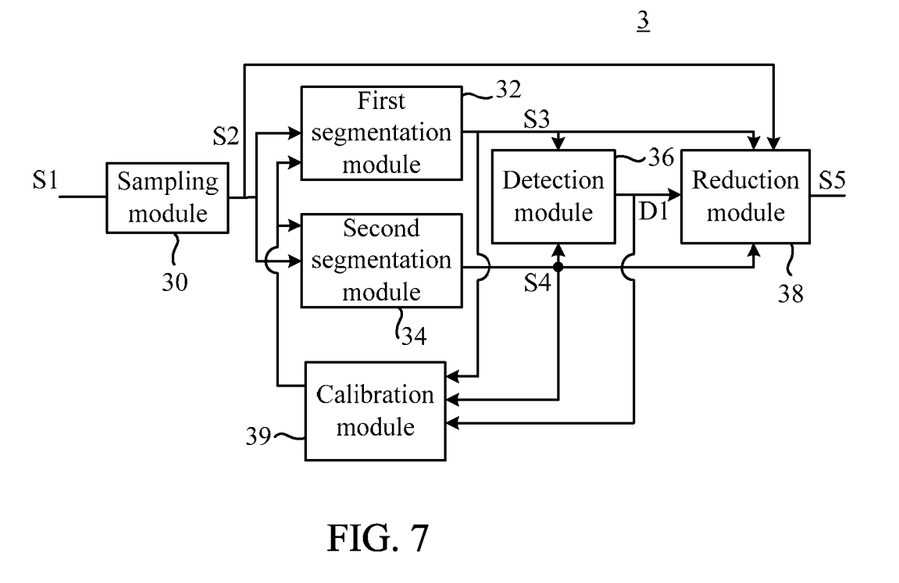
FIG. 7 shows a schematic diagram of a signal processing device according to another embodiment of the invention.

Please refer to FIG. 7. FIG. 7 shows a schematic diagram of a signal processing device according to another embodiment of the invention. As shown in FIG. 7, the signal processing device 3 includes a sampling module 30, a first segmentation module 32, a second segmentation module 34, a detection module 36, a reduction module 38 and a calibration module 39. The sampling module 30 samples an input signal S1 to generate a sample signal S2. The first segmentation module 32 receives the sample signal S2 to calculate a plurality of first segment values S3 during respective first time intervals. The second segmentation module 34 receives the sample signal S2 to calculate a plurality of second segment values S4 during respective second time intervals. The detection module 36 generates a detection signal D1 according to the determination of whether the first segment values S3 lies out a first range and whether a corresponding contemporary second segment values S4 lies out a second range. The reduction module 38 is controlled by the detection signal D1 to generate an output signal S5. The calibration module 39 couples to the detection module 36, the first segmentation module 32, and the second segmentation module 34 to receive the plurality of first segment values S3, the plurality of the second segment values S4 and the detection signal D1. The calibration module 39 then adjusts the first range, the second range, the first time interval and/or the second time interval according to the plurality of first segment values S3, the plurality of second segment values S4 and the detection signal D1.

As an example showing operation of the calibration module 39, considering the input signal S1 is an ECG signal. Upon startup of the signal processing device 3, the plurality of first segment values S3 and the plurality of second segment values S4 are monitored by the calibration module 39. Typically, during this startup procedure, the patients may be asked to stay inactive physically, e.g. lie down on a bed, to get a resting ECG signal. In this situation, the calibration module 39 can set up initial values of the first range, the second range, the first time interval and the second time interval to the signal processing device 3.

Secondly, the calibration module 39, during a normal operation procedure, continues monitoring the plurality of first segment values S3, the plurality of second segment values S4 and the detection signal D1 so as to adjust the first range, the second range, the first time interval and/or the second time interval. During this normal operation procedure, there might be some noise or morphology variation affecting the input signal. For example, if the detection signal indicates the input signal S1 has a disease-like pattern frequently, the first time interval and the second time interval may be adjusted by the calibration module 39 to have longer period than the original settings. In this way, the plurality of first segment values and the plurality of second segment values are not likely to exceed the first range and the second range too easily. The detection module 36 will be less sensitive to the morphology variation, and the reduction module 38 may at least not tend to enter into the first state to perform noise reduction filtering. Thus, the morphology of the first signal S1 can be preserved from distortion.

On the other hand, if the input signal S1 is indicated to have a noise-like pattern, the first time interval and the second time interval may be adjusted to have shorter period than the original settings, so that the detection module 36 can be more sensitive to the noise. Therefore, the reduction module 38 might be more likely to enter into the first or second state to perform noise reduction filtering and the noise component might be more easily removed from the input signal S1.

Figure 8:
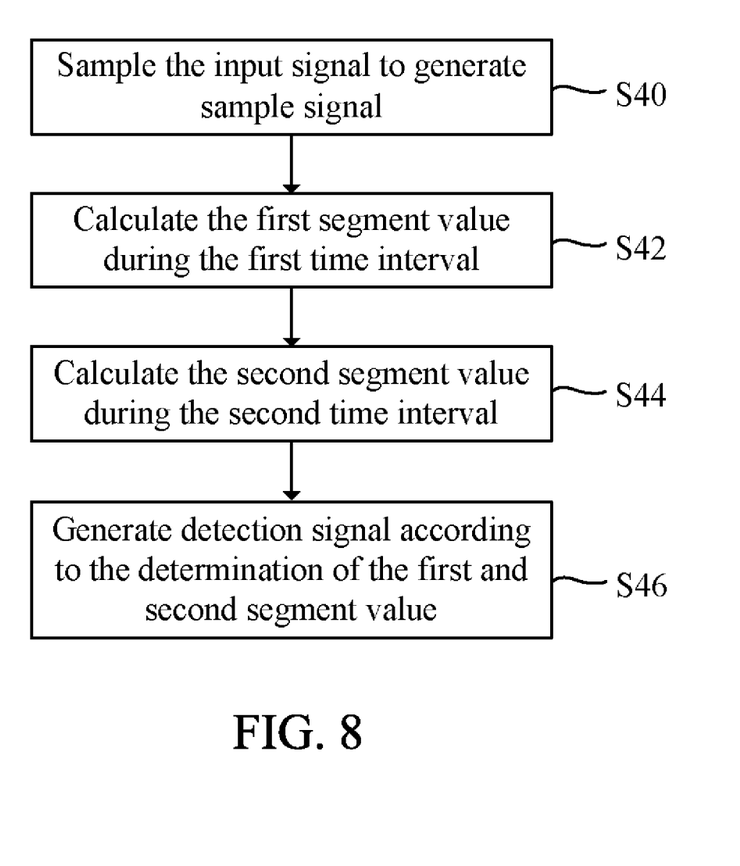
FIG. 8 shows a flow chart of a signal processing method according to an embodiment of the invention.

In order to explain how the signal processing device 1 works, please refer to FIG. 1 and FIG. 8. FIG. 8 shows an example flow chart of a signal processing method according to an embodiment of the invention. As shown in figures, in step S40, the sampling module 10 samples the input signal S1 to generate the sample signal S2. In step S42, the first segmentation module 12 calculates the first segment value during the first time interval. In step S44, the second segmentation module 14 calculates the second segment value during the second time interval different in length from the first time interval. Note that step S42 and step S44 may be performed concurrently. In step S46, the detection module 16 generates the detection signal according to the determination of whether the first segment value lies out of the first range, and whether the second segment value lies out of a second range.

To sum up, the embodiments of the invention disclose a method and a device for signal processing which can reduce the noise components of a specific signal, especially the ECG signal. One of the advantages of the approach is that users can easily and correctly analyze the waveform profile between successive heartbeats in the filtered ECG signal, and can avoid misdiagnosing the level of cardiac stability.

The descriptions illustrated supra set forth simply the preferred embodiments of the present invention; however, the characteristics of the present invention are by no means restricted thereto. All changes, alternations, or modifications conveniently considered by those skilled in the art are deemed to be encompassed within the scope of the present invention delineated by the following claims.

What is claimed is:

1. A signal processing device, comprising:
   a sampling module configured to sample an input signal to generate a sample signal;
   a first segmentation module configured to calculate a first segment value according to the sample signal during a first time interval, wherein the first segmentation module calculates sample data of the sample signal within the first time interval to derive the first segment value;
   a second segmentation module configured to calculate a second segment value according to the sample signal during a second time interval, wherein the second segmentation module calculates sample data of the sample signal within the second time interval to derive the second segment value, and the length of the first time interval is different from that of the second time interval; and
   a detection module, coupled to the first segmentation module and the second segmentation module, configured to generate a detection signal according to the determination of whether the first segment value lies out of a first range, and whether the second segment value lies out of a second range.

2. The signal processing device according to claim 1, further comprising:
   a baseline tracking unit, coupled to the first segmentation module and the second segmentation module, for generating an estimated baseline signal according to one of the first segment value and the second segment value.

3. The signal processing device according to claim 2, further comprising:
   an adaptive filter, coupled to the baseline tracking unit and the detection module, for generating an output signal according to the estimated baseline signal, the sample signal and a first step size while the first segment value lies out of the first range, and the second segment value lies out of the second range.

4. The signal processing device according to claim 2, further comprising:
   an adaptive filter, coupled to the baseline tracking unit and the detection module, for generating an output signal according to the estimated baseline signal, the sample signal and a second step size while either the first segment value lies within the first range, or the second segment value lies within the second range.

5. The signal processing device according to claim 2, further comprising:
   an adder, coupled to the baseline tracking unit, for generating an output signal by subtracting the estimated baseline signal from the sample signal.

6. The signal processing device according to claim 1, wherein the first segmentation module calculates a plurality of first segment values during a plurality of first time intervals and the second segmentation module calculates a plurality of second segment values during a plurality of second time intervals, each of the plurality of second time intervals overlapping with more than one, but not limited to an integer multiple, of the plurality of first time intervals.

7. The signal processing device according to claim 6, further comprising:
   a calibration module configured to adjust the first range, the second range, the first time interval and the second time interval according to the plurality of first segment values, the plurality of second segment values, and the detection signal.

8. A signal processing method, comprising:
   sampling an input signal to generate a sample signal;
   calculating a first segment value according to the sample signal during a first time interval, wherein the step of calculating the first segment value according to the sample signal during the first time interval comprises:
      calculating sample data of the sample signal within the first time interval to derive the first segment value;
   calculating a second segment value according to the sample signal during a second time interval, wherein the length of the first time interval is different from that of the second time interval, and the step of calculating the second segment value according to the sample signal during the second time interval comprises:
      calculate sample data of the sample signal within the second time interval to derive the second segment value; and
   generating a detection signal according to the determination of whether the first segment value lies out of a first range, and whether the second segment value lies out of a second range.

9. The signal processing method according to claim 8, further comprising:
   generating an estimated baseline signal according to one of the first segment value and the second segment value.

10. The signal processing method according to claim 9, further comprising:
    generating an output signal according to the estimated baseline signal, the sample signal and a first step size while the first segment value lies out of the first range, and the second segment value lies out of the second range.

11. The signal processing method according to claim 9, further comprising:
    generating an output signal according to the estimated baseline signal, the sample signal and a second step size while either the first segment value lies within the first range, or the second segment value lies within the second range.

12. The signal processing method according to claim 9, further comprising:
    generating an output signal by subtracting the estimated baseline signal from the sample signal.

13. The signal processing method according to claim 8, wherein a plurality of first segment values are calculated during a plurality of first time intervals and a plurality of second segment values are calculated during a plurality of second time intervals, each of the plurality of second time intervals overlapping with more than one of the plurality of first time intervals.

14. The signal processing method according to claim 13, further comprising:
    adjusting the first range, the second range, the first time interval and the second time interval according to the plurality of first segment values, the plurality of second segment values, and the detection signal.

15. A signal processing device, comprising:
    a sampling module configured to sample an input signal to generate a sample signal;
    a first segmentation module configured to calculate a first segment value according to the sample signal during a first time interval, wherein the first segmentation module calculates sample data of the sample signal within the first time interval to derive the first segment value;

a second segmentation module configured to calculate a second segment value according to the sample signal during a second time interval, wherein the second segmentation module calculates sample data of the sample signal within the second time interval to derive the second segment value, and the length of the first time interval is different from that of the second time interval; and a reduction module coupled to the first segmentation module and the second segmentation module, configured to generate an output signal according to the sample signal, the first segment value and the second segment value.

16. The signal processing device according to claim 15, wherein the reduction module comprises:

a baseline tracking unit, coupled to the first segmentation module and the second segmentation module, for generating an estimated baseline signal according to one of the first segment value and the second segment value.

17. The signal processing device according to claim 16, wherein the reduction module further comprises:

an adaptive filter, coupled to the baseline tracking unit, for generating the output signal according to the estimated baseline signal, the sample signal and a step size.

18. The signal processing device according to claim 16, wherein the reduction module further comprises:

an adder, coupled to the baseline tracking unit, for generating the output signal by subtracting the estimated baseline signal from the sample signal.

19. The signal processing device according to claim 15, wherein the first segmentation module calculates a plurality of first segment values during a plurality of first time intervals and the second segmentation module calculates a plurality of second segment values during a plurality of second time intervals, each of the plurality of second time intervals overlapping with more than one, but not limited to an integer multiple, of the plurality of first time intervals.

* * * * *